(12) United States Patent
Sunaoka et al.

(10) Patent No.: US 7,154,274 B2
(45) Date of Patent: Dec. 26, 2006

(54) HIGH-SENSITIVITY MEASURING INSTRUMENT AND METHOD OF USING THE INSTRUMENT TO MEASURE A CHARACTERISTIC VALUE AT A POINT IN TIME

(75) Inventors: Yoshio Sunaoka, Tokyo (JP); Shinichi Ohashi, Tokyo (JP); Toshio Morita, Tokyo (JP); Masashi Fujita, Tokyo (JP)

(73) Assignee: Organo Corporation, Tokyo (JP)

( * ) Notice: Subject to any disclaimer, the term of this patent is extended or adjusted under 35 U.S.C. 154(b) by 57 days.

(21) Appl. No.: 10/508,225

(22) PCT Filed: Mar. 19, 2003

(86) PCT No.: PCT/JP03/03370

§ 371 (c)(1),
(2), (4) Date: Sep. 20, 2004

(87) PCT Pub. No.: WO03/078989

PCT Pub. Date: Sep. 25, 2003

(65) Prior Publication Data

US 2005/0110499 A1 May 26, 2005

(30) Foreign Application Priority Data

Mar. 20, 2002 (JP) .............................. 2002-078067

(51) Int. Cl.
*G01N 27/02* (2006.01)

(52) U.S. Cl. .................. 324/439; 324/444; 324/617
(58) Field of Classification Search ............... 324/439
See application file for complete search history.

(56) References Cited

U.S. PATENT DOCUMENTS 5,444,379 A * 8/1995 Ohmi et al. ................ 324/450
6,646,443 B1 * 11/2003 Higo .......................... 324/439
6,690,172 B1 * 2/2004 Higo .......................... 324/439

* cited by examiner

*Primary Examiner*—Walter Benson
(74) *Attorney, Agent, or Firm*—Norris McLaughlin & Marcus PA (57) ABSTRACT

A high-sensitivity measuring instrument comprising at least two sensors for detecting the same characteristics by touching a substance being measured with a specified time difference, wherein the between detection signals taken out simultaneously from respective sensors is determined, the difference between characteristic values upon elapsing the specified time difference is determined from the difference between detection signals, a reference time of measurement and a reference characteristic value at that time are preset, a time axis having a time pitch of a specified time difference is set, and a measurement value is obtained at a point in time elapsing an arbitrary time pitch from the reference time. Objective measurement characteristics can be detected by the measuring instrument not in the form of difference or variation but as an absolute value with high accuracy and sensitivity.

7 Claims, 5 Drawing Sheets

HIGH-SENSITIVITY MEASURING INSTRUMENT AND METHOD OF USING THE INSTRUMENT TO MEASURE A CHARACTERISTIC VALUE AT A POINT IN TIME

TECHNICAL FIELD OF THE INVENTION

The present invention relates to a high-sensitivity measuring instrument which detects a variation in characteristic of a substance being measured such as an aqueous solution with high sensitivity and accuracy, and can detect the characteristic value itself at that time with high sensitivity and accuracy based on the detected value of the variation in characteristic.

BACKGROUND ART OF THE INVENTION

As characteristics of a substance being measured, for example, an electric conductivity is used as, in particular, a scale for measuring a concentration of an ion capable of moving in an aqueous solution, and an electric conductivity measuring instrument is used for measurement of ion concentration of many aqueous solutions. Generally, the electric conductivity measuring instrument determines increase/decrease of ion concentration of an aqueous solution being measured by measuring a resistance between a detection electrode and an electrode for supplying a current from a power source.

In a case where a variation of electric conductivity or a difference in electric conductivity between a plurality of positions being measured is determined by using a conventional electric conductivity measuring instrument, when the variation or the difference is small as compared with an absolute value of the electric conductivity being measured, because the measurement range of the instrument is being adjusted for a relatively large absolute value of electric conductivity, the measurement of a fine variation or difference is very difficult, or the measurement data are very poor in reliability. In practice, however, there are much demands for determining such a fine difference or variation between two or more measurement points different from each other in position or in time, and if such a fine difference or variation can be measured with a high reliability and with high accuracy and sensitivity, such measurement would find wide application.

Accordingly, in order to satisfy the above-described demands, the applicant of the present invention previously proposed a multi-dimension electric conductivity measuring instrument in JP-A-2001-311710 as an instrument capable of abstracting and determining a variation of characteristics of a substance being measured such as an aqueous solution with a high accuracy. This multi-dimension electric conductivity measuring instrument comprises at least two electric conductivity measuring cells each having at least two electrodes coming into contact with a substance being measured, and the electric conductivity measuring cells are electrically connected to each other so that the detection signals themselves from the respective electric conductivity measuring cells are processed by at least addition or subtraction.

In this instrument, to the detection signals themselves from the respective electric conductivity measuring cells, namely, to the detection signals themselves abstracted simultaneously, the electrical processing such as addition or subtraction is carried out, and the signals after the processing, being amplified as needed, are outputted as a difference or a variation between measured electric conductivities of the respective electric conductivity measuring cells. Because a difference between detection signals abstracted simultaneously is outputted, it becomes possible to detect a variation with a high S/N ratio by erasing a noise commonly generated in the respective electric conductivity measuring cells, and it becomes possible to output only the difference or the variation at a high accuracy, by amplification, etc. Therefore, in this instrument, unlike an arrangement wherein a plurality of conventional electric conductivity measuring instruments are disposed and a difference or variation between the data measured therefrom is obtained, a fine difference or variation between electric conductivities of a plurality of measurement points different in position or in time from each other can be determined with a high reliability and with high accuracy and sensitivity.

Although the invention disclosed in the above-described JP-A-2001-311710 was proposed for measurement of electric conductivity, the technology by which a difference or variation in characteristics to be measured is determined with a high reliability and with high accuracy and sensitivity by outputting a difference between detection signals simultaneously taken out from at least two sensors, can be applied basically to measurement of any characteristic.

However, the indicated value in the multi-dimension electric conductivity measuring instrument proposed by the above-described JP-A-2001-311710 is a fine difference or variation between electric conductivities in a plurality of measurement points different in position or in time from each other, and such an indicated value is not an absolute value of electric conductivity. In practice, however, a variation in absolute value of electric conductivity is frequently required for measurement of variation in concentration of impurities in an aqueous solution, etc. Even when a characteristic other than the electric conductivity is determined, measurement of absolute value of the characteristic is frequently required.

DISCLOSURE OF THE INVENTION

Accordingly, paying attention to the fact that a fine difference or variation in characteristics of a substance being measured can be determined with a high accuracy by the technology proposed by the above-described JP-A-2001-311710, and assuming that such a technology is practical, an object of the present invention is to provide a measuring instrument which can further determine not a difference or variation but a measurement value of an objective characteristic with high accuracy and sensitivity, desirably, as an absolute value.

To accomplish the above object, a high-sensitivity measuring instrument according to the present invention comprises at least two sensors for detecting the same characteristics by bringing them into contact with a substance being measured with a specified time difference, wherein a difference between detection signals abstracted simultaneously from respective sensors is determined, a difference between characteristic values upon elapsing the specified time difference is determined from said difference between detection signals, a reference time of measurement and a reference characteristic value at that time are preset, a time axis having a time pitch of the specified time difference is set, and a measurement value is obtained at a point in time elapsing an arbitrary time pitch from the reference time.

In the above-described high-sensitivity measuring instrument, it is possible to obtain only a measurement value at a certain time as a value determined by adding an amount of variation from the reference time to the reference characteristic value at the reference time, and it is also possible to obtain measurement values as data in time sequence at respective points in time elapsing respective time pitches from the reference time.

Further, in a case of obtaining the measurement values as data in time sequence, the data in time sequence may comprise a plurality of groups of data in time sequence including data in time sequence, a position of a time pitch of which is present within the above-mentioned specified time difference. In such an embodiment, it is possible that the plurality of groups of data in time sequence can output measurement values at respective points in time elapsing respective time pitches in the direction of the time axis with a pitch smaller than the above-mentioned specified time difference, and it becomes possible to indicate the variation of the measurement value as if it were a continuous variation.

Further, in the above-described high-sensitivity measuring instrument, it is necessary to set a reference characteristic value at a reference time, and various methods for setting this reference characteristic value can be employed. For example, a substance being measured for reference is brought into contact with the sensors, and an output value thereof in the measuring instrument can be set as the reference characteristic value. In this case, even if the characteristic value of this substance being measured for reference is not known, by using a substance being measured for reference adequate for comparing it with an objective substance being measured, it becomes possible to determine what value the characteristic value of the objective substance being measured becomes relative to the characteristic value which the substance being measured for reference has, thereby obtaining at least a relative value compared with the substance being measured for reference.

Alternatively, it is also possible to bring a substance being measured for reference having a known characteristic value (for example, ultra pure water, etc.) into contact with the sensors, and to set the reference characteristic value so that an output value thereof becomes the known characteristic value in the measuring instrument according to the present invention. By thus contacting a substance being measured for reference having a known characteristic value, it becomes possible to calibrate the reference characteristic value with a high accuracy.

Therefore, by using a substance being measured for reference whose characteristic value is not known or a substance being measured for reference whose characteristic value is known as described above, for example, even in a case where there is a fear that an initially set reference characteristic value may drift with a lapse of a long period of time, it becomes possible to correct the drift at an appropriate interval in time, and whereby it becomes possible to carry out measurement or monitoring always at a high accuracy.

In the present invention, the substance being measured is not particularly restricted, but the present invention can be easily applied particularly to a case where it is a fluid.

In such a high-sensitivity measuring instrument according to the present invention, since firstly a difference between detection signals simultaneously abstracted from at least two sensors touching a substance being measured with a specified time difference is outputted, only a variation of an objective characteristic value at a certain time, for example, at the present time, is detected at high sensitivity and accuracy. The technical concept up to this step is substantially the same as that proposed in the aforementioned JP-A-2001-311710. In the present invention, further, a difference between characteristic values upon elapsing the specified time difference is determined from the above-described difference between the detection signals, a reference time of measurement and a reference characteristic value at that time are preset, the above-mentioned specified time difference is set as a time pitch, and a measurement value is obtained at a point in time elapsing an arbitrary time pitch from the reference time (namely, at a point in time elapsing an arbitrary time pitch at which an output as the measurement value is required). This measurement value is obtained as a value calculated by setting the reference characteristic value as a reference of the measurement, and as long as an absolute value is set as the reference characteristic value, the measurement value is obtained also as an absolute value of characteristic value. In other words, the above-described variation in time of the characteristic detected at high sensitivity and accuracy at the specified time difference is added to the reference characteristic value at the reference time, and the finally outputted signal indicates a variation of the absolute value of the characteristic detected precisely at this variation in time, and it becomes possible to detect the target absolute value itself at a high sensitivity and a high accuracy.

Namely, in the high-sensitivity measuring instrument according to the present invention, it becomes possible to determine a variation of characteristic of a substance being measured at a high sensitivity and a high accuracy, in particular, as an absolute value. Therefore, an absolute value of a measurement value having a generality can be outputted, and using this output, a characteristic value can be monitored at high sensitivity and accuracy, and a detailed determination becomes possible by applying a general data processing method utilized in various fields at the present time such as a determination due to wave analysis or time integral of variation.

THE BEST MODE FOR CARRYING OUT THE INVENTION

Hereinafter, desirable embodiments of the present invention will be explained referring to the drawings.

In the present invention, the characteristic of a substance being measured, which is a target for measurement, is not limited to electric conductivity, and the present invention can be applied to measurement of substantially any characteristic, but the following explanation will be described mainly with respect to a case of measurement of electric conductivity.

Figure 1:
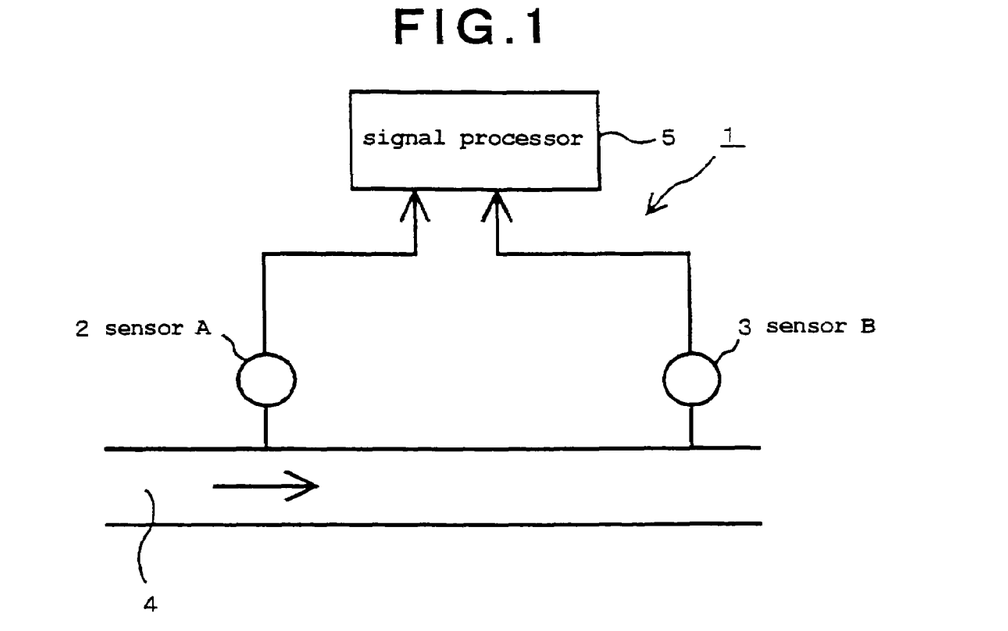
FIG. 1 is a schematic diagram showing an example of installation of a high-sensitivity measuring instrument according to an embodiment of the present invention.
Figure 2:
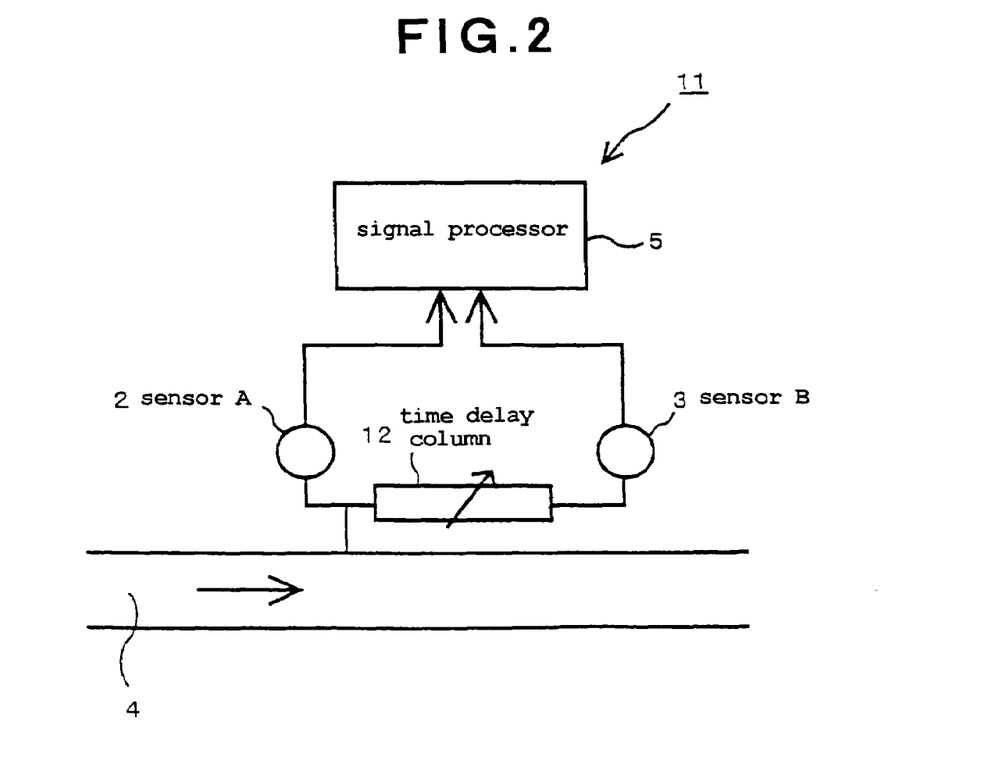
FIG. 2 is a schematic diagram showing another example of installation of a high-sensitivity measuring instrument according to an embodiment of the present invention.

FIGS. 1 and 2 exemplify cases where a high-sensitivity measuring instrument according to the present invention is applied to an electric conductivity measurement system for a fluid, for example, water flowing in a pipe as a substance being measured 4. In a high-sensitivity measuring instrument 1 shown in FIG. 1, sensor A (2) and sensor B (3) for detecting electric conductivity are provided respectively at the upstream side and the downstream side of the substance being measured 4. The substance being measured 4 through sensor A and also passes through sensor B, that is, the substance being measured 4 comes into contact with sensors A and B with a specified time difference, and it is possible that detection signals from both sensors are taken out simultaneously. In a signal processor 5 provided are a multi-dimension electric conductivity measuring instrument capable of outputting a difference between detection signals taken out from both sensors simultaneously at a certain time (exemplified in FIGS. 3 and 4), and a calculation processing part wherein using the difference as a difference between characteristic values at that time and at a time before or after the above-described time difference (namely, as a difference between characteristic values upon elapsing the specified time difference), a reference time of measurement and a reference characteristic at that time are preset, a time axis having a time pitch of the specified time difference is set, and a measurement value can be obtained at a point in time elapsing an arbitrary time pitch from the reference time.

In a high-sensitivity measuring instrument 11 shown in FIG. 2, a sample water sampled from an identical position as an object for measuring electric conductivity comes into contact with sensor A (2) as it is, and comes into contact with sensor B (3) via a time delay column 12 capable of being adjusted in time, and a specified time difference is given through the time delay column 12. Other structure is substantially the same as that of the embodiment shown in FIG. 1.

First, examples of constitution of a multi-dimension electric conductivity measuring instrument provided in signal processor 5 will be explained referring to FIGS. 3 and 4. In a multi-dimension electric conductivity measuring instrument 21 shown in FIG. 3, at least two sensors A and B (2, 3) for measurement of electric conductivity each having at least two electrodes (in this embodiment, shown as a three-electrode structure) touching a substance being measured are provided. In this embodiment, respective sensors A and B (2, 3) are electrically connected so that the detection signals themselves from the respective sensors are processed by addition.

Respective sensors A and B (2, 3) are connected electrically in parallel to each other, an AC current is supplied from an AC oscillator 24 provided as a power source to electrodes 22a, 23a of the respective sensors for current supply at a condition of the same phase. Electrodes 22b, 23b of respective sensors A and B (2, 3) for electric conductivity detection are electrically connected to each other, and the values of the detection signals themselves from both detection electrodes 22b and 23b are added to each other. Further, in this embodiment, a multiplier or divider 25 for multiplying the value of the supplied current at a predetermined magnification or for dividing it at a predetermined rate is provided at a position before electrode 22a for current supply to one sensor A (2), and it is possible to differentiate the level of the electric conductivity of a substance being measured to be detected by sensor A (2) as compared with that of sensor B (3). Namely, an AC current before being supplied to electrode 22a for current supply is amplified or attenuated at a predetermined magnification. In such a structure, it becomes possible to detect a variation in time of electric conductivity of a substance being measured, which comes into contact with the respective sensors with a specified time difference, at an optimum sensitivity.

The above-described processed signals, that is, the signals obtained from electrodes 22b and 23b for electric conductivity detection are amplified as an output signal having an adequate level by a single amplifier 26. At that time, an optimum range depending upon an objective measurement can be selected by a measurement range switching device 27.

In this embodiment, the signal from amplifier 26, after a temperature compensation for measurement environment is carried out by a temperature compensator 28, is synchronized with the output side of AC oscillator 24, and further, is amplified by an amplifier 31 with a range adjustor 30 so that the signal becomes a signal having a level optimum for control or output display to be employed, and the signal is taken out as an actual output 32.

Figure 3:
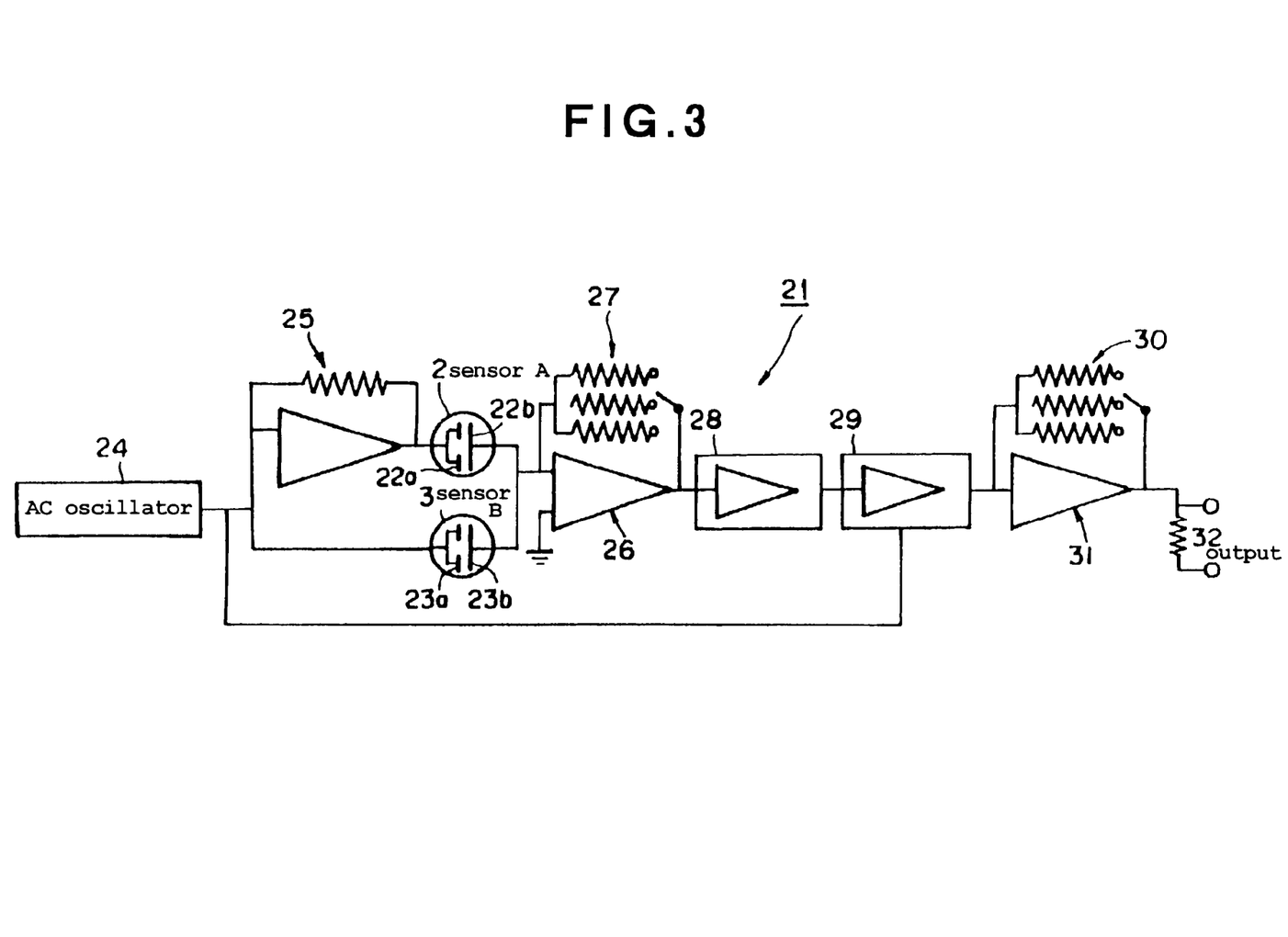
FIG. 3 is a circuit diagram showing an example of constitution of a multi-dimension electric conductivity measuring instrument provided in a signal processor of the instrument depicted in FIGS. 1 and 2.
Figure 4:
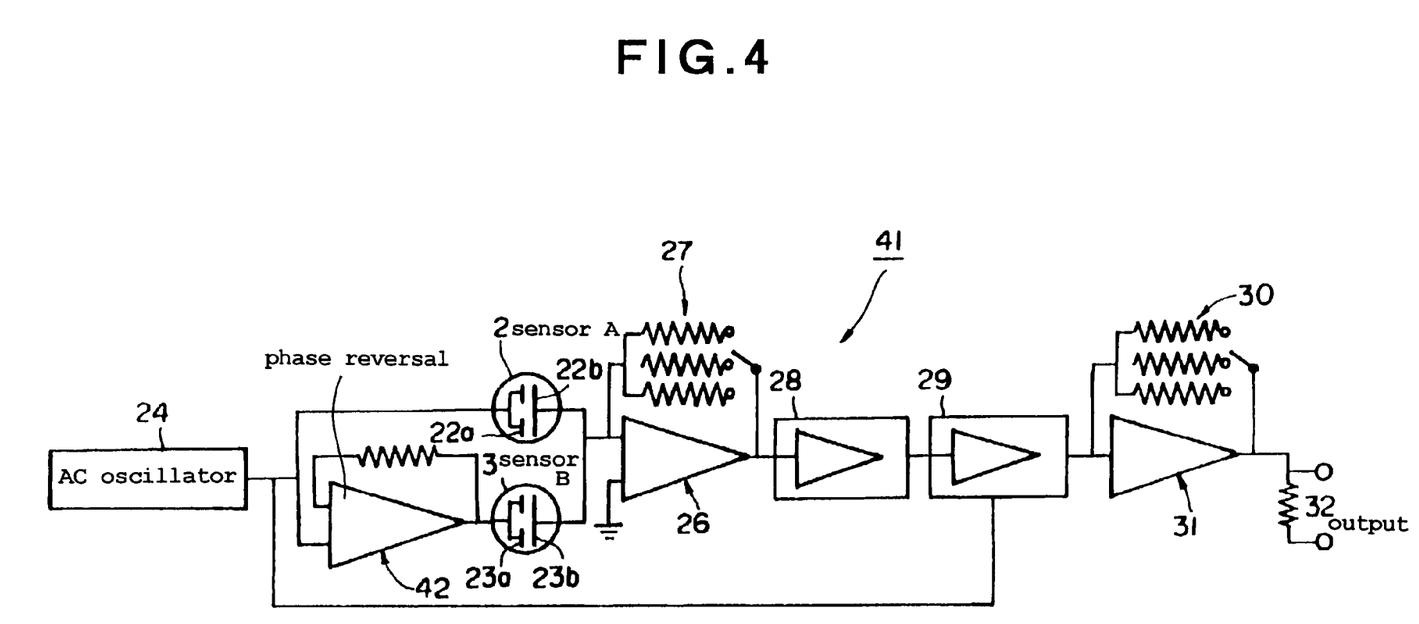
FIG. 4 is a circuit diagram showing another example of constitution of a multi-dimension electric conductivity measuring instrument provided in a signal processor of the instrument depicted in FIGS. 1 and 2.

In a multi-dimension electric conductivity measuring instrument 41 shown in FIG. 4, as compared with the embodiment shown in FIG. 3, a multiplier or divider 42 for multiplying the value of the supplied current at a predetermined magnification or for dividing it at a predetermined rate is provided at a position before electrode 23a for current supply of sensor B (3), and it is possible to differentiate the level of the electric conductivity of a substance being measured to be detected by sensor B (3) as compared with that of sensor A (2). Namely, an AC current before being supplied to electrode 23a for current supply is amplified or attenuated at a predetermined magnification. The multiplier or divider has also a function to reverse the phase of the supplied AC current. In such a structure, the detection signals themselves from respective sensors A, B (2, 3) are substantially processed by subtraction, and the signal after the subtraction processing is sent to amplifier 26. The structure of other parts is substantially the same as that of the embodiment shown in FIG. 3.

In the above-described multi-dimension electric conductivity measuring instruments 21 and 41, since the detection signals from sensors A, B (2, 3) are taken out simultaneously at a certain time, and a difference between the simultaneously taken-out signals is outputted, it becomes possible to remove an influence ascribed to outside disturbance or noise, and only the above-described difference is outputted at a high accuracy and a high sensitivity. In the present invention, using this output of the difference, the following processing is carried out in the calculation processing part provided in signal processor 5. Namely, the above-described difference is used as a difference between characteristic values upon elapsing a specified time difference, a reference time of measurement and a reference characteristic value at that time are preset, a time axis having a time pitch of the specified time difference is set, and a measurement value is obtained at a point in time elapsing an arbitrary time pitch from the reference time.

The basic concept of this calculation processing will be explained.

In the above, because a signal difference ($D_{A-B}(t)$) between a signal of sensor A ($F_A(t)$) and a signal of sensor B ($F_B(t)$) at a certain time is obtained and the signal of sensor B ($F_B(t)$) indicates an absolute value of a characteristic (electric conductivity in the above-described embodiment) at a point before elapsing the specified time difference, the following equation stands.

$$F_A(t) = D_{A-B}(t) + F_B(t) \qquad (1)$$

In practice, there is a case where $F_A(t)$, $F_B(t)$ and $D_{A-B}(t)$ are not in a same data line, and therefore it is necessary to mutually convert the data depending on the utilization method when calculating these data, but this does not affect the essence of the present invention. Therefore, the indication is simplified in order to facilitate the explanation.

The inventors of the present invention paid attention to the fact that the signal difference $D_{A-B}(t)$ corresponds to the time difference between sensor A and sensor B, and considered that by utilizing this correspondence, a sensor sole signal, that is, a signal corresponding to an absolute value of characteristic can be derived. In the present invention, the above-described difference (that is, $D_{A-B}(t)$) is treated as a variation in time of a signal as if the signal were detected by a single sensor between at that time and at a time before or after that time by the aforementioned time difference. Namely, when a specified time difference between sensors A and B is referred to as DT, $D_{A-B}(t)$ is used as a difference of characteristic value at a point upon expiring DT. A time axis is set by setting this DT as a time pitch, and relatively to the reference characteristic value preset at the reference time, a measurement value at a point in time elapsing an arbitrary time pitch from the reference time is calculated as follows.

The relationship between $F_A$ and $F_B$ is represented as follows by using the specified time difference DT between sensors A and B.

$$F_B(t) = F_A(t - DT) \qquad (2)$$

From the equations (1) and (2), the following equation is led.

$$F_A(t) = D_{A-B}(t) + F_A(t - DT) \qquad (3)$$

Namely, the signal ($F_A(t)$) of sensor A at an arbitrary time t becomes a signal calculated by adding a signal difference between sensors A and B ($D_{A-B}(t)$) to a signal of sensor A at a point before the time of DT($F_A(t-DT)$). By this, it becomes possible to treat the value obtained by the equation (3) as an absolute value signal detected by a single hypothetical sensor.

Further, because the equation:

$$F_A(t - DT) = D_{A-B}(t - DT) + F_A(t - 2DT)$$

is derived, the following equation stands.

$$F_A(t) = D_{A-B}(t) + D_{A-B}(t - DT) + F_A(t - 2DT)$$

Further, because the equation:

$$F_A(t - 2DT) = D_{A-B}(t - 2DT) + F_A(t - 3DT)$$

is derived, the following equation stands.

$$F_A(t) = D_{A-B}(t) + D_{A-B}(t - DT) + D_{A-B}(t - 2DT) + F_A(t - 3DT)$$

By repeating similar operations, the following equation stands.

$$F_A(t) = (D_{A-B}(t) + D_{A-B}(t - DT) + D_{A-B}(t - 2DT) + \ldots + D_{A-B}(t - nDT)) + F_A(t - (n+1)DT)$$

Where, although $(D_{A-B}(t) + D_{A-B}(t-DT) + D_{A-B}(t-2DT) + \ldots + D_{A-B}(t-nDT))$ is obtained by adding up the signal differences of $D_{A-B}(t-iDT)$ provided as a general equation (i=0–n, "n" is a number of DT up to reach a previous certain reference time) by a time pitch of DT, even if traced back to any point, finally $F_A(t-(n+1)DT)$ is left.

Therefore, in the present invention, it is supposed to input a certain known value into $F_A(t-(n+1)DT)$. Namely, by inputting a value at an initial step of the above-described calculation as a reference characteristic value, it becomes possible to calculate a signal of only the sensor as a relative value relative to this reference characteristic value. If a reference value is an absolute value of a characteristic, a value added with the above-described variation can also be obtained as an absolute value of the characteristic to be measured as an object, and a variation of absolute value itself can be outputted. Although any value may be used as this reference characteristic value as long as the value is a known value, usually, it is understandable to employ a value, at a state where a signal difference between sensors A and B is zero at a condition that a particular signal does not enter, as the reference value. Further, as aforementioned, it is also possible to set a value whose absolute value is not known as a comparative reference value for calculating a measurement value, that is, the above-described reference characteristic value.

In the above-described calculation, it is also possible to calculate a signal of a sole sensor at a certain time, or to output sensor signals in order accompanying with time expiration, by analyzing after data collection. The steps are as follows for example.

(1) Setting of Parameter:

In a case of digital processing, although a time pitch within a DT time theoretically can be set arbitrarily, usually it is easy to set a time pitch at an equal interval. Further, if an appropriate analog circuit can be assembled, it may be employed. Hereinafter, a digital processing case will be explained wherein a time pitch within a DT time is set at an equal interval.

The time pitch within a DT time is referred to as "δt" and an arbitrary time "t" on a time axis is indicated as t=mDT+nδt. Where, "m" and "n" are integers, and "n" is 0–N, N=DT/δt.

By this, at an arbitrary time "t", the signal of sensor A is $F_A(mDT+n\delta t)$, the signal of sensor A is $F_B(mDT+n\delta t)$, and a signal difference is $D_{A-B}(mDT+n\delta t)$.

A signal of a sole sensor to be determined is referred to as $X(mDT+n\delta t)$.

Where, a parameter capable of being observed is $D_{A-B}(mDT+n\delta t)$, for example, due to the aforementioned multi-dimension electric conductivity measuring instrument.

(2) Input of Initial Value

A initially set known value is inputted at least as DT time, and a known value is set as a reference characteristic value at a reference time in data series of a sole sensor signal.

Here, the initial known reference characteristic value is set to be zero. Therefore, at m=0, X(nδt)=0 at n=0–N.

(3) Measurement

When a value before DT time is used, the following equation stands.

$$X(mDT+n\delta t) = X((m-1)DT+n\delta t) + (D_{A-B}(mDT+n\delta t)) \qquad (4)$$

When determined from the initial value, the following equation stands.

$$X(mDT+n\delta t) = X(n\delta t) + (\text{integral of } i=1-m \text{ of } D_{A-B}(iDT+n\delta t)) \qquad (5)$$

Thus, data in time sequence at respective points in time elapsing respective time pitches from the reference time can be obtained as data of measurement values, and the data in time sequence can comprise a plurality of groups of data in time sequence which are obtained by dividing with a pitch of δt smaller than the specified time difference DT.

(4) Storing of Data

In the above-described procedure, in a case of equation (4), it can be processed by storing N data of X(mDT+nδt) within a immediately previous time DT. In a case of equation (5), although it is necessary to store all previous data of X(mDT+nδt), in this case, it is possible to indicate all past data.

Figure 5:
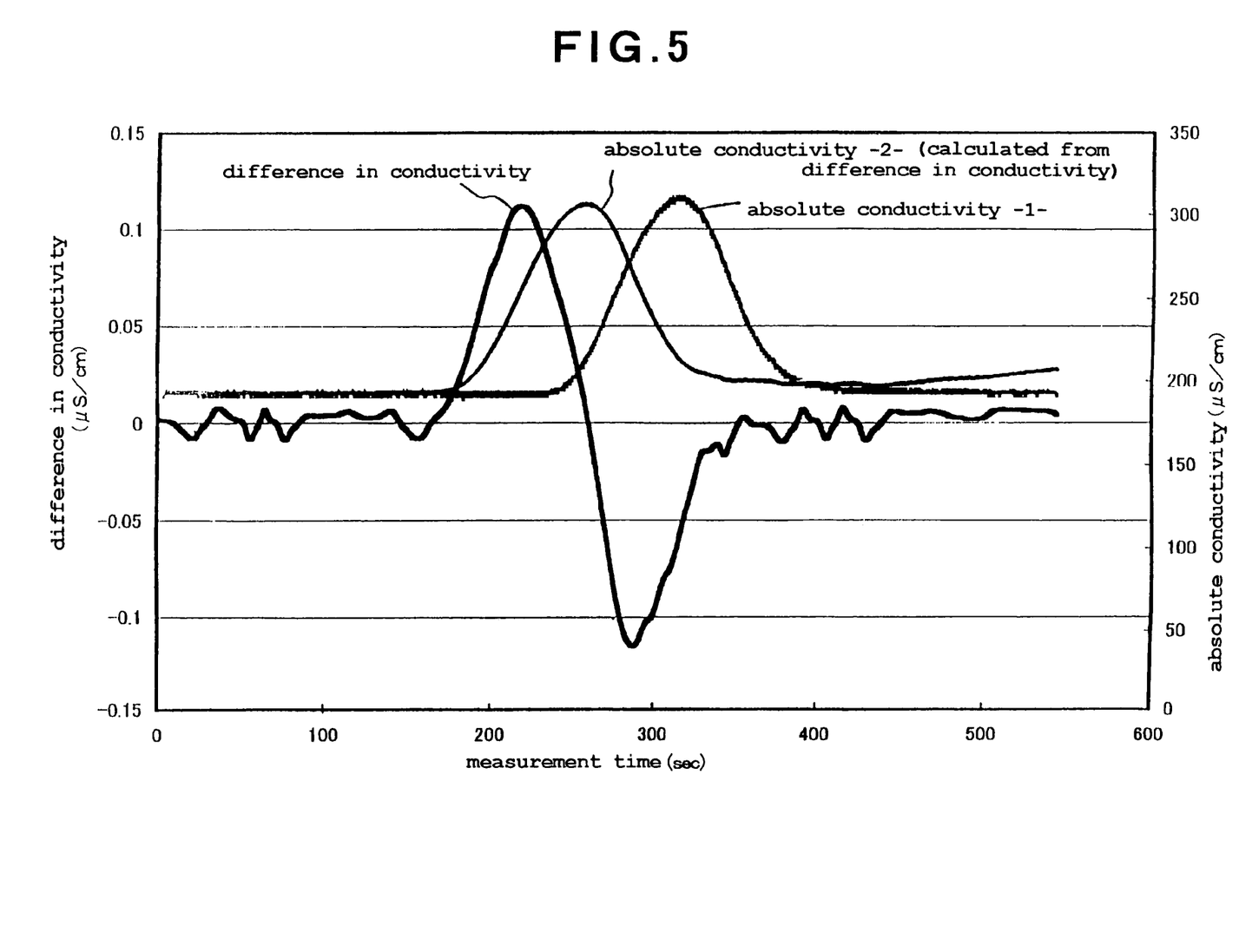
FIG. 5 is a chart showing a result of a test carried out for confirming the performance of a high-sensitivity measuring instrument according to the present invention.
Figure 6:
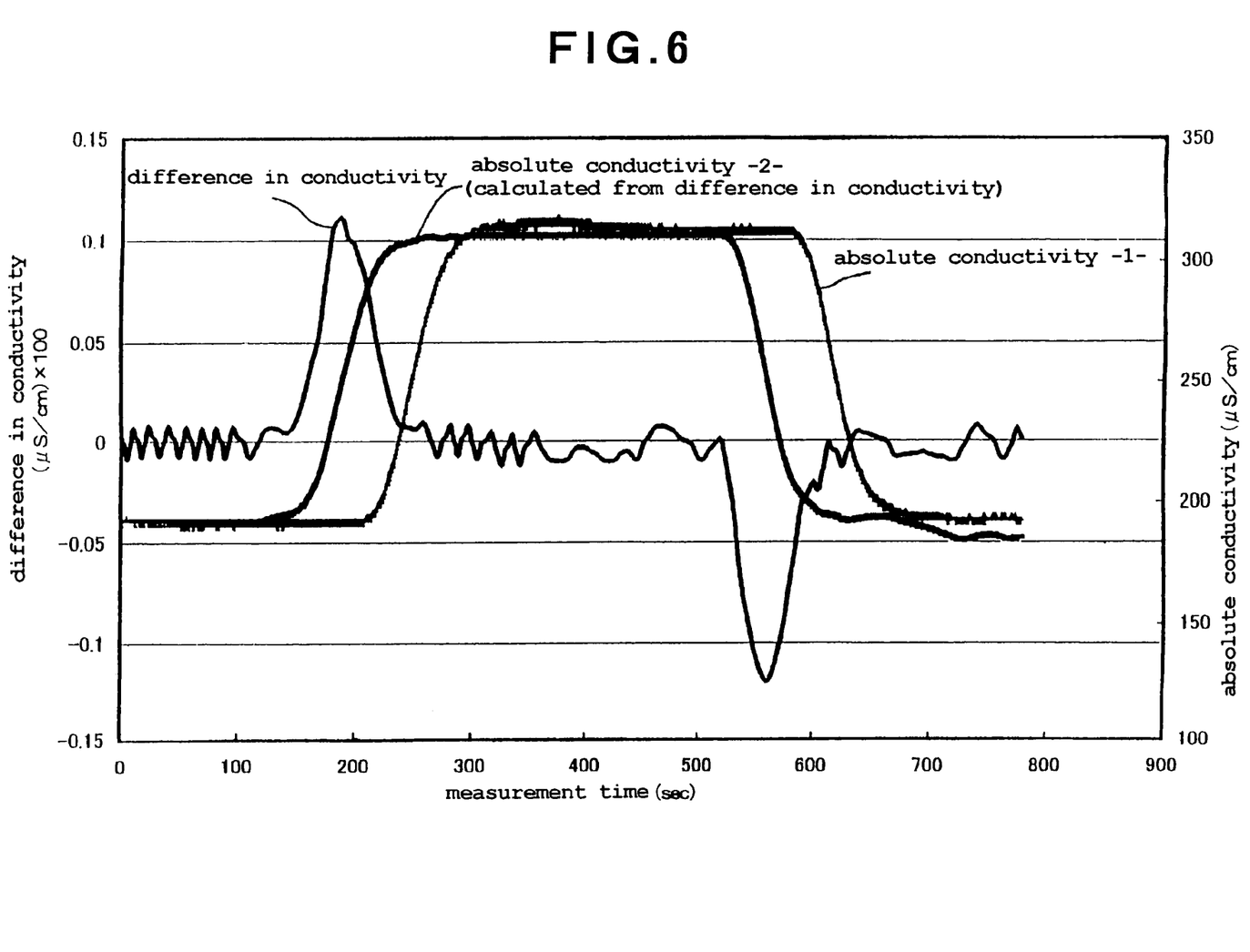
FIG. 6 is a chart showing a result of another test carried out for confirming the performance of a high-sensitivity measuring instrument according to the present invention.

By carrying out the above-described calculation, for example, the measurement in a measurement system as shown in FIG. 1 has been carried out. The result of the measurement is shown in FIGS. 5 and 6. FIG. 5 shows an example of measurement in a case where a temporary variation of electric conductivity occurred, and FIG. 6 shows an example of measurement in a case where a variation of electric conductivity with a certain continuous time occurred. In FIGS. 5 and 6, "a difference in conductivity" indicates only a variation of electric conductivity outputted from a difference signal of sensors A and B, and "an absolute conductivity -1-" is an electric conductivity detected by a sensor provided at a downstream position separately from sensors A and B and is outputted for confirming the effectiveness of the present invention. "An absolute conductivity -2- (calculated from difference in conductivity)" indicates an absolute value of electric conductivity as an objective high-sensitivity measurement value which is calculated by adding the difference in conductivity to the above-described preset reference characteristic value.

In both FIGS. 5 and 6, the absolute conductivity -2- extremely precisely indicates substantially the same characteristic as the characteristic measured as the absolute conductivity -1-, and it is understood that the measurement by the high-sensitivity measuring instrument according to the present invention has been carried out at a high sensitivity. Further, in the high-sensitivity measuring instrument according to the present invention, because it is possible that a difference between detection signals of sensors A and B outputted as a high-accuracy observation value is outputted as an absolute value added to a known reference value, the accuracy of the absolute value as the outputted measurement value can also be maintained surely at a high level. Namely, a high-sensitivity and high-accuracy measurement becomes possible.

Although the above-described explanation has been carried out mainly as to the measurement of electric conductivity, the high-sensitivity measuring instrument according to the present invention can be applied not only to this, but also to basically any measurement system requiring the determination of a variation of an absolute value of an objective characteristic to be measured or a relative variation from a certain reference value as the case may be. Therefore, the present invention can be applied to any measuring instrument requiring a high-sensitivity measurement at an excellent S/N ratio, for example, a measurement of ultra-violet ray, a measurement of differential refractive index, a measurement of fluorescent luminous intensity, an electrochemical measurement, a measurement of fine particles, etc.

INDUSTRIAL APPLICATIONS OF THE INVENTION

The high-sensitivity measuring instrument according to the present invention can be applied to any measurement system requiring a determination of a variation of an absolute value of an objective characteristic to be measured or a relative variation from a certain reference value. The high-sensitivity measuring instrument according to the present invention exhibits remarkable advantages when it is used particularly as a detector in ion chromatography or liquid chromatography requiring a high-sensitivity measurement of characteristics in a fluid at a high S/N ratio, or as a monitor for observing a minute concentration of impurities contained in a ultra pure water.

The invention claimed is:

1. A high-sensitivity measuring instrument comprising:
   a) at least two sensors adapted to detect the same characteristic of a substance brought into contact with said sensors; and
   b) a signal processor operably linked to both of said at least two sensors;
   wherein said at least two sensors are positioned so that they contact the substance at different times characterized by a specified time difference; and
   wherein the signal processor calculates a difference between detection signals taken out simultaneously from said at least two sensors, calculates a difference between characteristic values upon elapsing said specified time difference, presets a reference characteristic value at that reference time, sets a time axis having a time pitch of said specified time difference, and calculates a measurement value at a point in time elapsing an arbitrary time pitch from said reference time.

2. The high-sensitivity measuring instrument according to claim 1, wherein data in time sequence at respective points in time elapsing respective time pitches from said reference time are obtained as data of measurement values.

3. The high-sensitivity measuring instrument according to claim 2, wherein said data in time sequence comprise a plurality of groups of data in time sequence including data in time sequence, a position of a time pitch of which is present within said specified time difference.

4. The high-sensitivity measuring instrument according to claim 1, wherein a substance being measured for reference is brought into contact with said sensors, and an output value thereof in said measuring instrument is set as said reference characteristic value.

5. The high-sensitivity measuring instrument according to claim 1, wherein a substance being measured for reference having a known characteristic value is brought into contact with said sensors, and said reference characteristic value is set so that an output value thereof in said measuring instrument becomes said known characteristic value.

6. The high-sensitivity measuring instrument according to claim 1, wherein said substance being measured is a fluid.

7. A method for measuring a characteristic value of a substance at a given point in time, said method comprising:
   a) providing the high-sensitivity measuring device according to claim 1;
   b) bringing the at least two sensors into contact with said substance; and
   c) processing detection signals from said at least two sensors in said signal processor to give a measurement of the characteristic value of the substance at a given point in time.

* * * * *